(12) United States Patent
Brauner et al.

(10) Patent No.: US 8,794,758 B2
(45) Date of Patent: Aug. 5, 2014

(54) RETRACTABLE EARPLUG APPARATUS FOR AN EYEWEAR ASSEMBLY AND A VEST ASSEMBLY

(75) Inventors: Bill E. Brauner, Angels Camp, CA (US); Eivind Clausen, Bellingham, WA (US)

(73) Assignee: ReadyMax, Inc., Elk Grove, CA (US)

( * ) Notice: Subject to any disclaimer, the term of this patent is extended or adjusted under 35 U.S.C. 154(b) by 396 days.

(21) Appl. No.: 12/908,802

(22) Filed: Oct. 20, 2010

(65) Prior Publication Data

US 2011/0094007 A1 Apr. 28, 2011

Related U.S. Application Data

(60) Provisional application No. 61/254,149, filed on Oct. 22, 2009.

(51) Int. Cl.
*G02C 5/14* (2006.01)

(52) U.S. Cl.
USPC .................................................. 351/123; 2/13

(58) Field of Classification Search
None
See application file for complete search history.

(56) References Cited

U.S. PATENT DOCUMENTS

| | | | | |
|---|---|---|---|---|
| 2,501,107 A * | 3/1950 | Volkmann | ..................... | 381/378 |
| 3,384,903 A * | 5/1968 | Malcom, Jr. | ..................... | 2/434 |
| 3,943,925 A * | 3/1976 | Leight | ..................... | 128/866 |
| 4,901,355 A * | 2/1990 | Moore | ..................... | 381/381 |
| RE35,051 E * | 10/1995 | Moore | ..................... | 381/381 |
| 5,475,449 A * | 12/1995 | Pyle | ..................... | 351/123 |
| 5,581,821 A * | 12/1996 | Nakano | ..................... | 2/422 |
| 5,703,670 A * | 12/1997 | Callard | ..................... | 351/123 |
| 5,715,323 A * | 2/1998 | Walker | ..................... | 381/385 |
| 5,781,272 A * | 7/1998 | Bright et al. | ..................... | 351/123 |
| 6,067,664 A | 5/2000 | Cortes | | |
| 6,074,060 A * | 6/2000 | Bruce | ..................... | 351/158 |
| 6,082,855 A * | 7/2000 | Fleming | ..................... | 351/123 |
| 6,176,576 B1 * | 1/2001 | Green et al. | ..................... | 351/123 |
| 6,340,227 B1 * | 1/2002 | Solberg et al. | ..................... | 351/123 |
| 6,565,208 B1 * | 5/2003 | Lee | ..................... | 351/122 |
| 6,690,807 B1 * | 2/2004 | Meyer | ..................... | 381/327 |
| 6,905,206 B2 * | 6/2005 | Skuro | ..................... | 351/118 |

(Continued)

OTHER PUBLICATIONS

International Search Report dated Apr. 22, 2009 from International Application No. PCT/US2009/033242.

(Continued)

*Primary Examiner* — Richale Quinn

(74) *Attorney, Agent, or Firm* — Beyer Law Group LLP

(57) ABSTRACT

An eyewear temple arm apparatus for an eyewear device including an elongated body member having a proximal end portion configured to mount to the eyewear device. The temple arm apparatus includes a functional element, an elongated flexible tether; and a guide base. The base is movably mounted to the elongated body member for movement thereof along a fixed path in a direction generally longitudinally therealong between a first position and a second position. In the first position, the guide base is positioned proximate to a proximal portion of the body member, while in the second position, it is oriented proximate to a distal portion thereof. One end of the tether is mounted to the guide portion and an opposite end thereof is mounted to the functional element such that when guide base is moved between the first and second positions, the functional element is moved between a parked condition, parked relative to the body member, and an operational condition, positioning the functional element sufficiently away from the body member to enable operation thereof.

22 Claims, 11 Drawing Sheets

(56) References Cited

U.S. PATENT DOCUMENTS

| | | | |
|---|---|---|---|
| 7,150,526 B2 * | 12/2006 | Jannard et al. | 351/158 |
| 7,344,243 B2 * | 3/2008 | Skuro | 351/156 |
| D587,679 S * | 3/2009 | Komiyama | D14/205 |
| D593,067 S * | 5/2009 | Millora et al. | D14/205 |
| 7,810,750 B2 * | 10/2010 | Abreu | 242/378.1 |
| D666,287 S * | 8/2012 | Quinlan | D24/106 |
| 8,378,924 B2 * | 2/2013 | Jacobsen et al. | 345/7 |
| 2002/0098877 A1 * | 7/2002 | Glezerman | 455/568 |
| 2003/0079935 A1 | 5/2003 | Weise | |
| 2007/0229755 A1 * | 10/2007 | Duane | 351/158 |
| 2007/0248238 A1 * | 10/2007 | Abreu | 381/381 |
| 2008/0143954 A1 * | 6/2008 | Abreu | 351/158 |
| 2010/0319714 A1 * | 12/2010 | Oshima et al. | 128/858 |
| 2011/0051982 A1 * | 3/2011 | Abreu | 381/384 |

OTHER PUBLICATIONS

Written Opinion dated Apr. 22, 2009 from International Application No. PCT/US2009/033242.

* cited by examiner

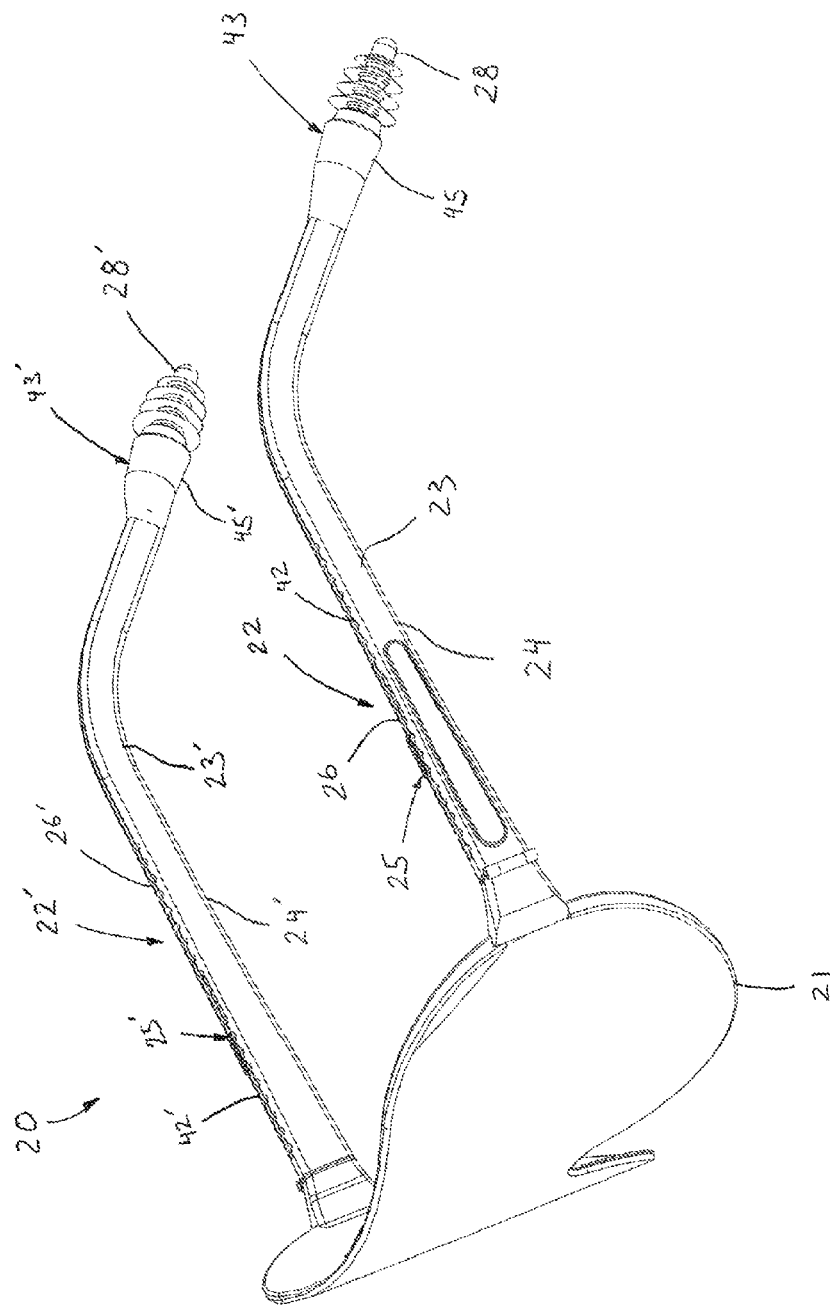
FIG._1

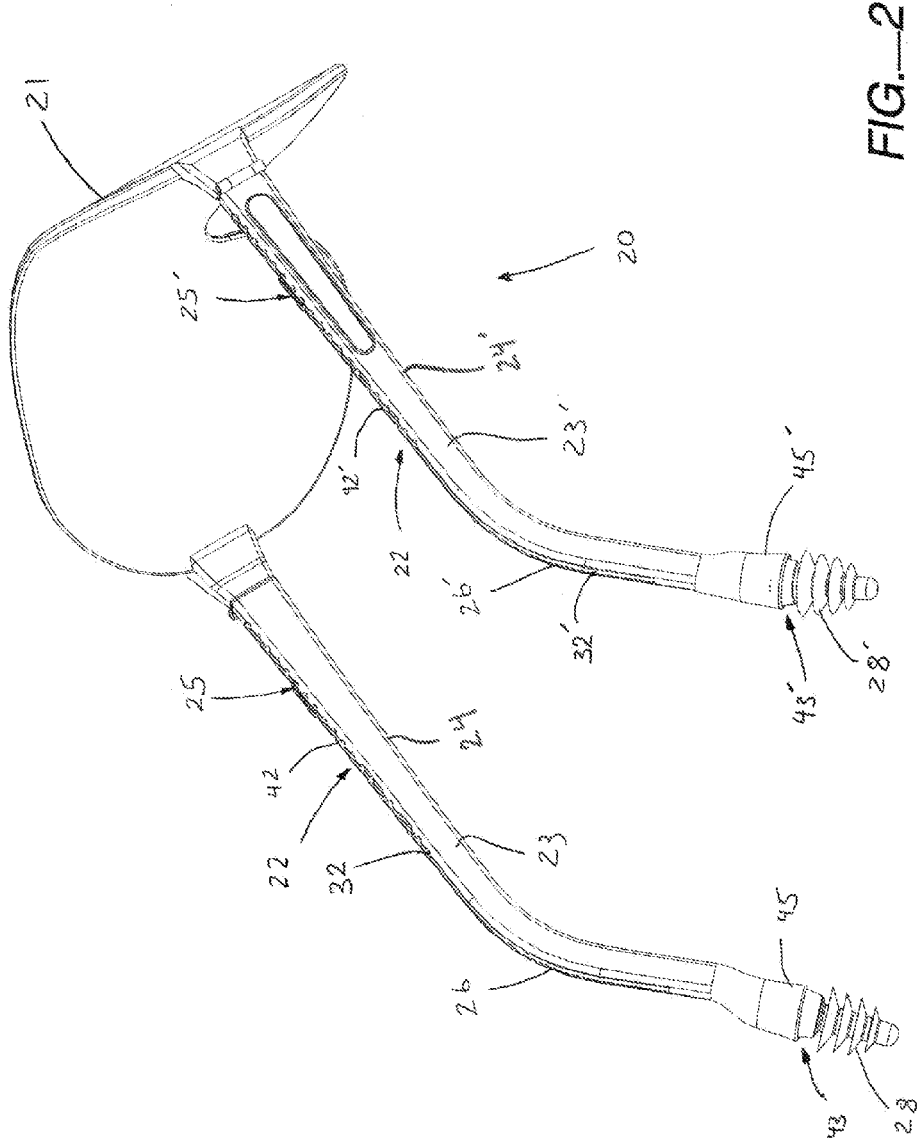
FIG._2

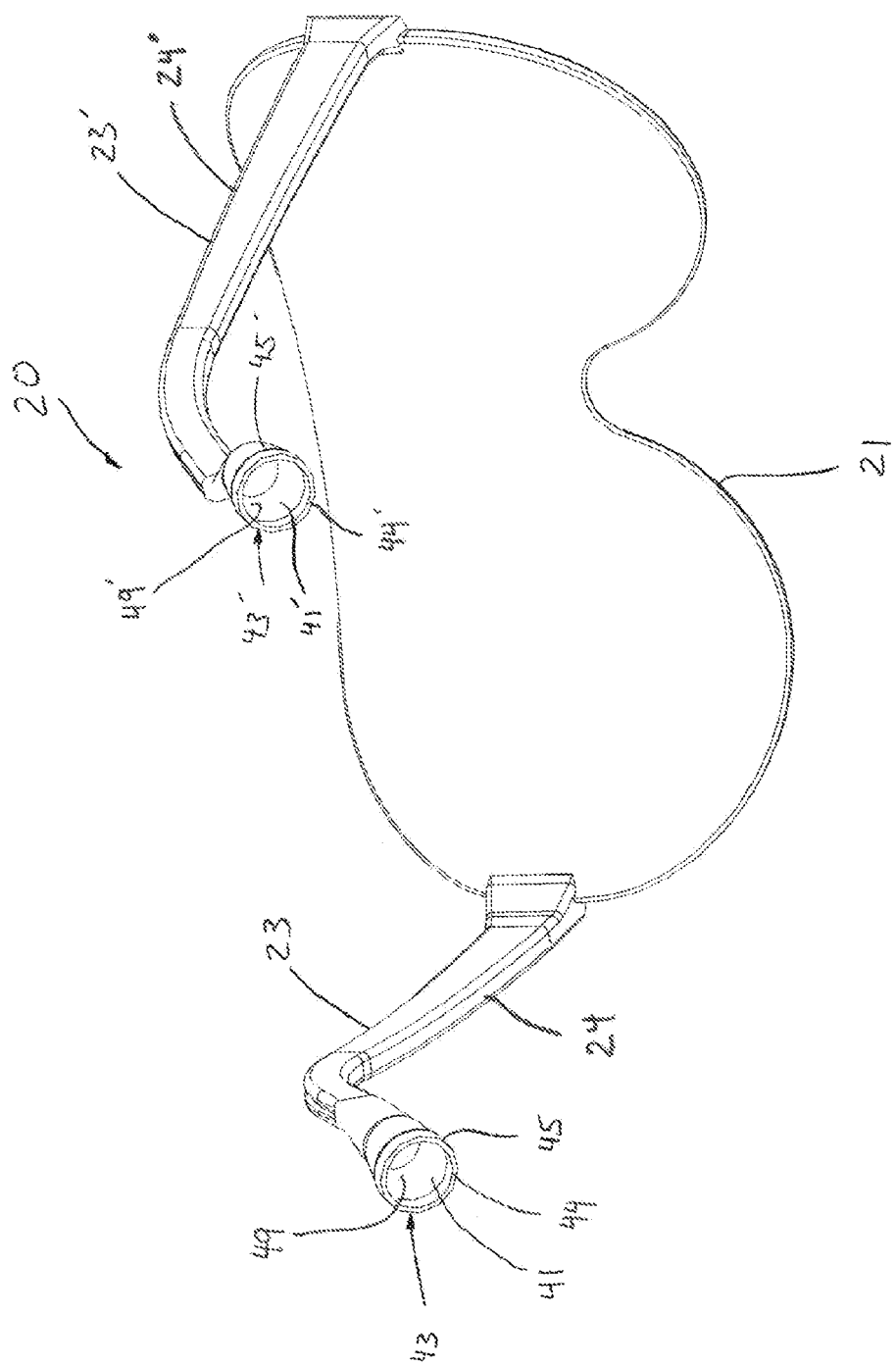
FIG._3

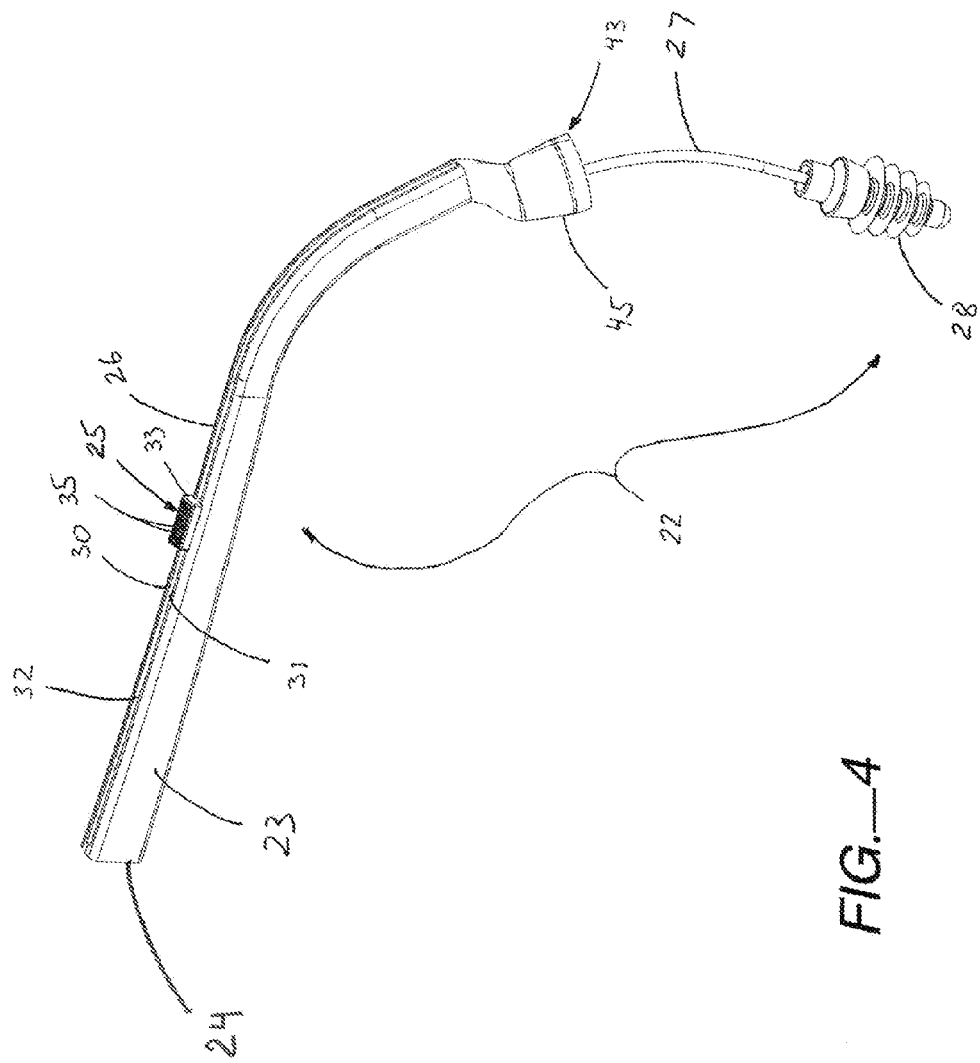
FIG._4

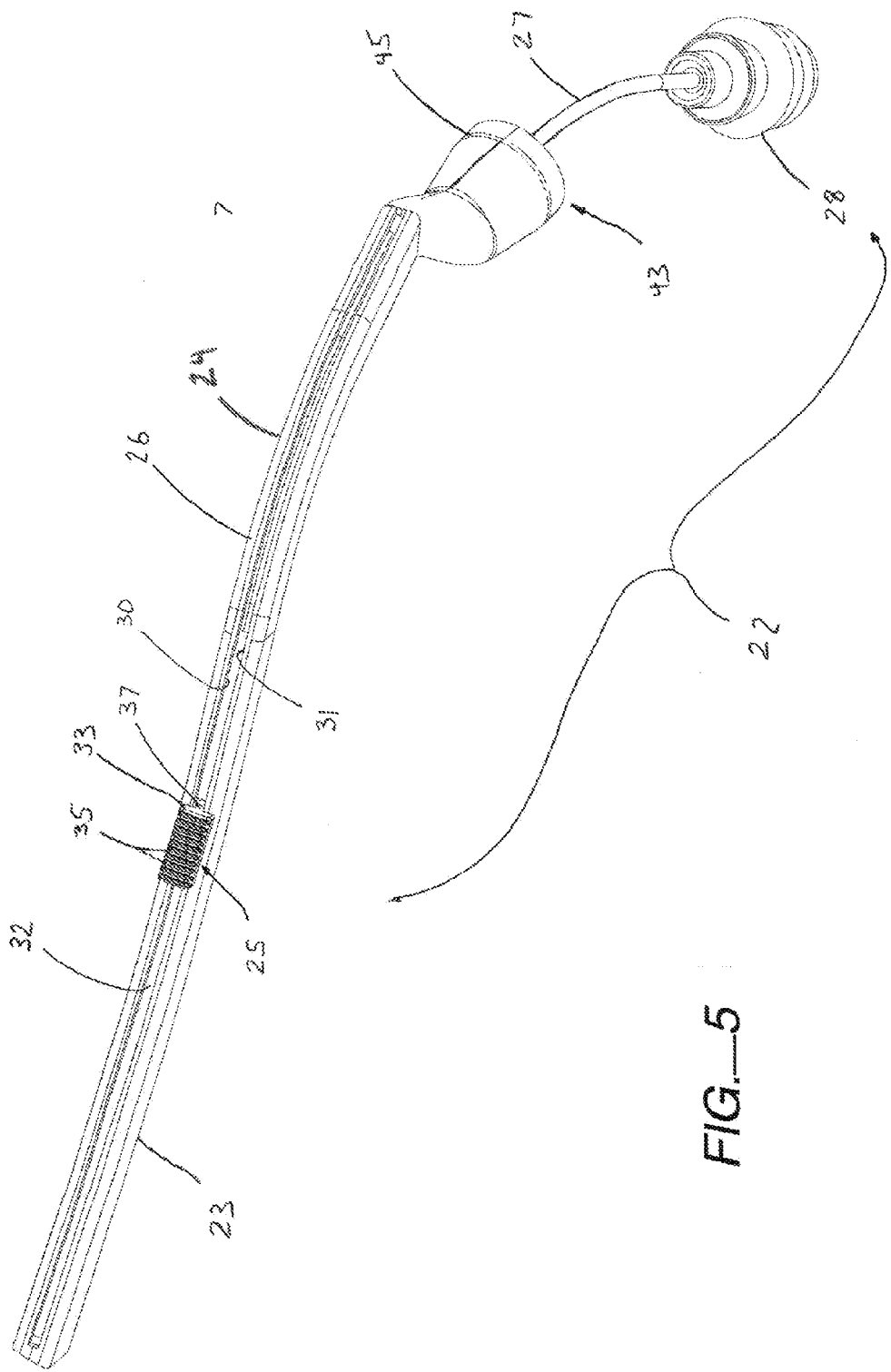
FIG._5

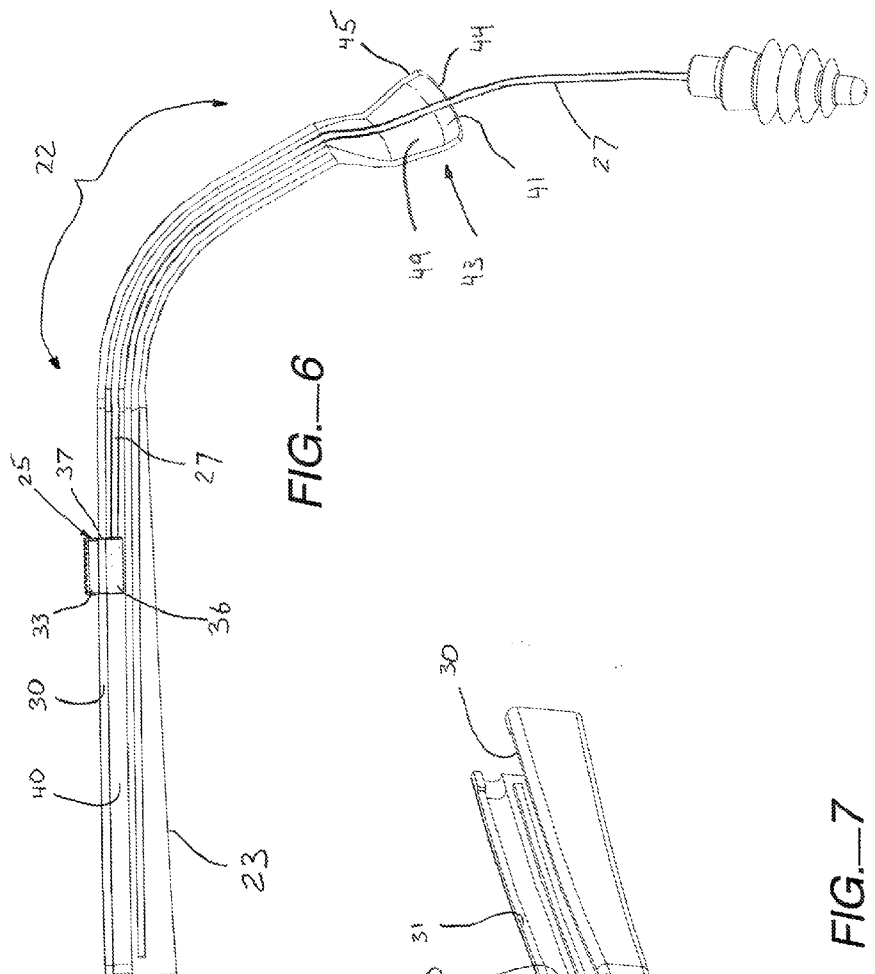
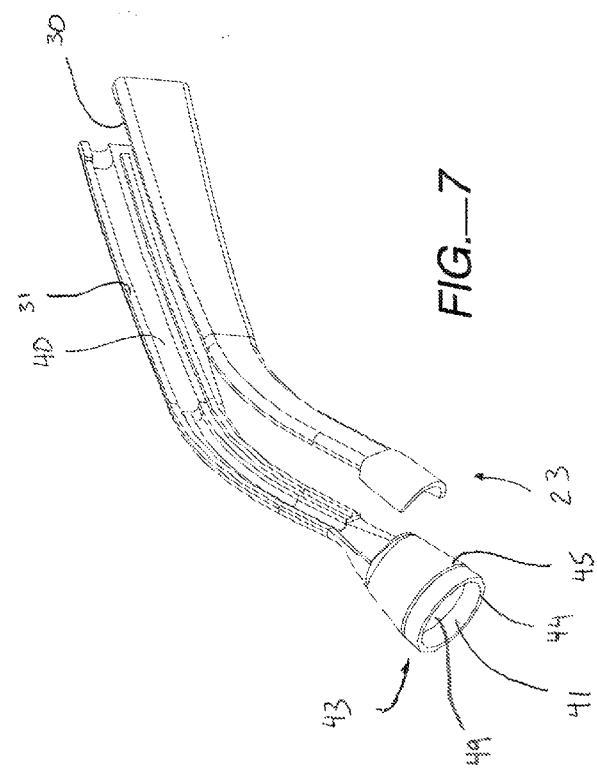

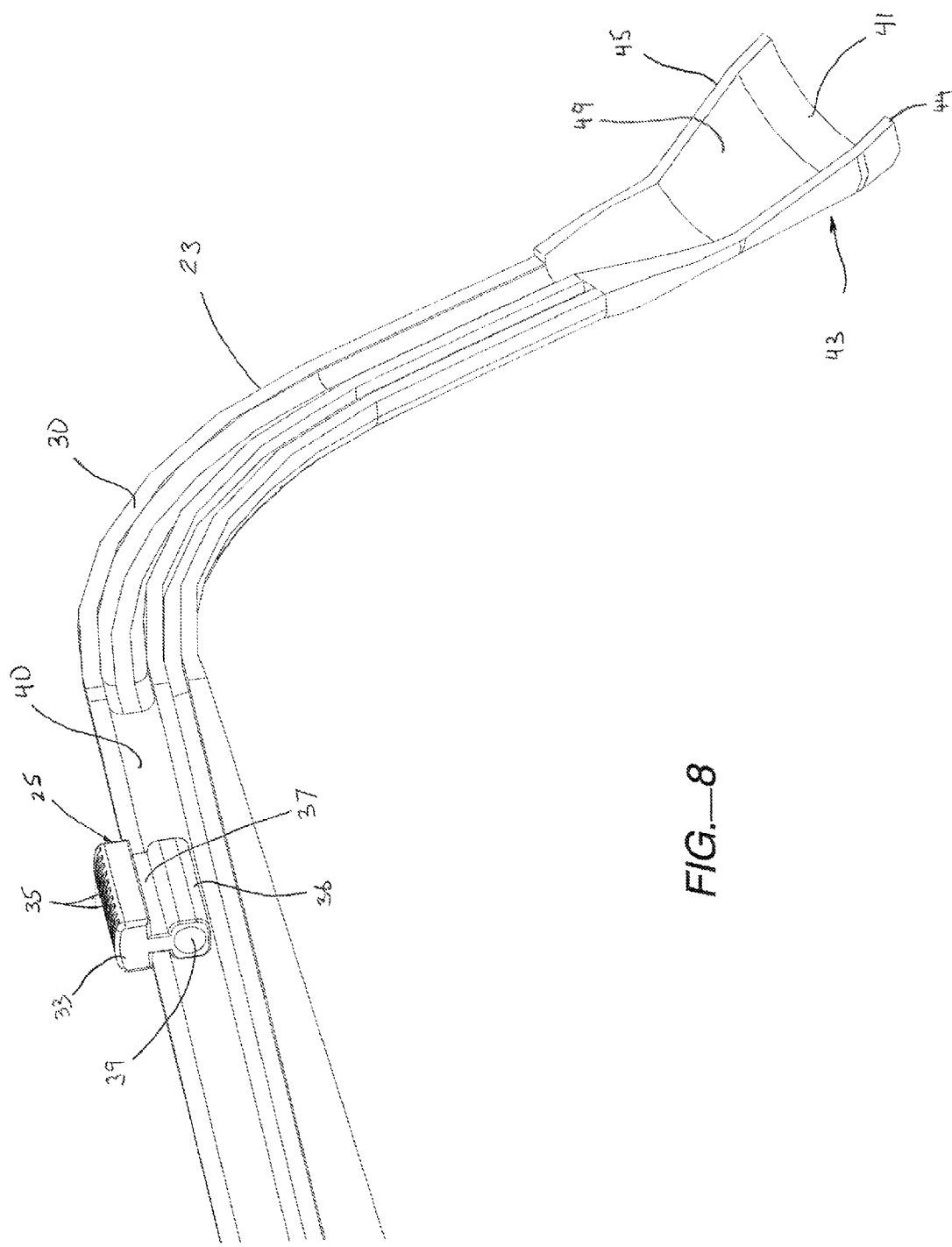
FIG._8

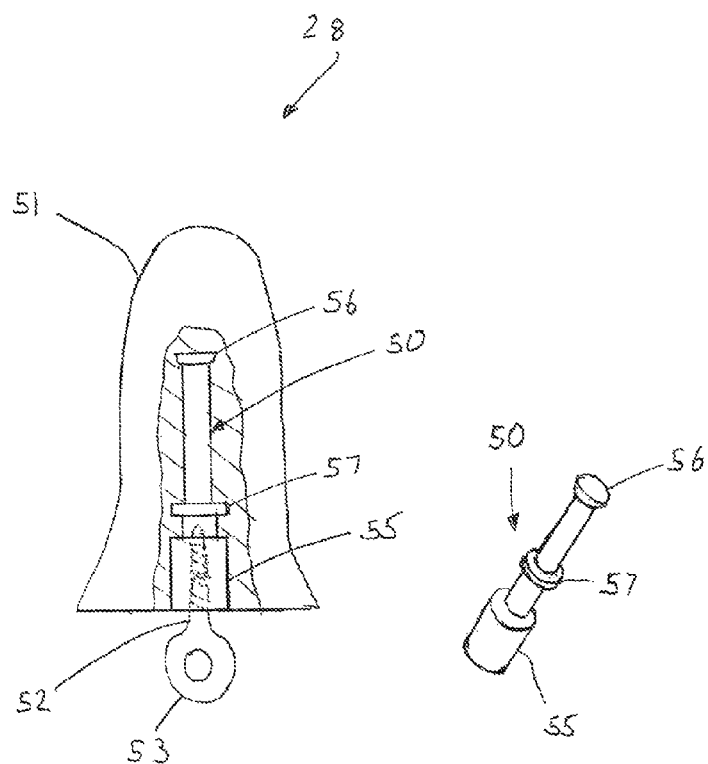
FIG._9   FIG._10

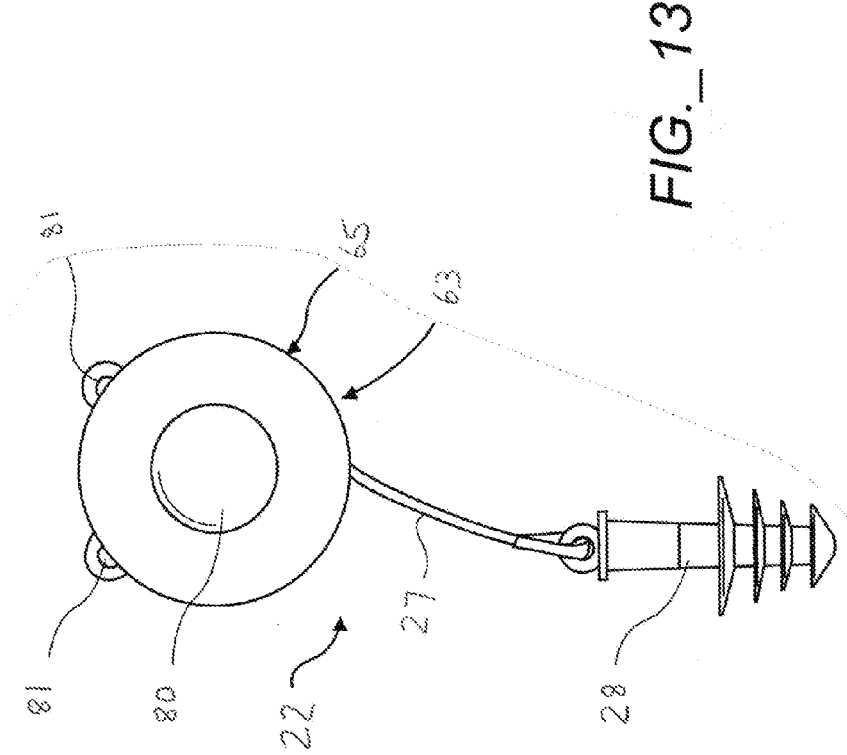
FIG._13
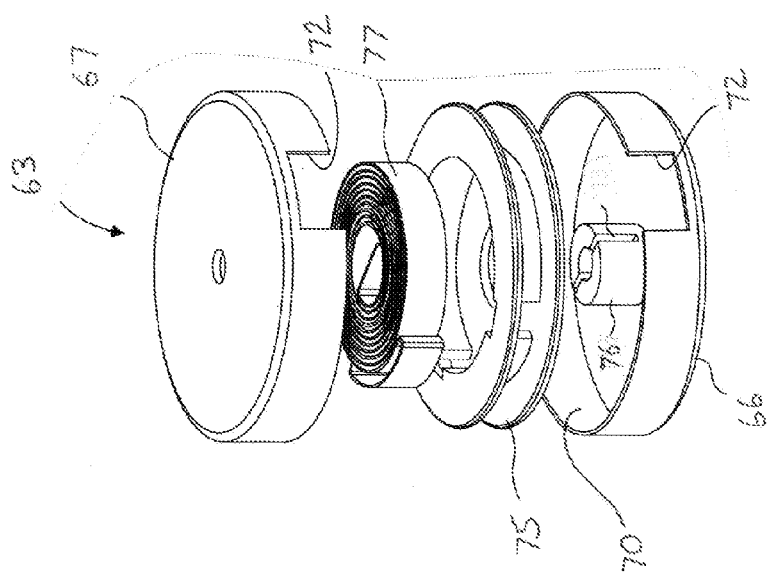
FIG._14

RETRACTABLE EARPLUG APPARATUS FOR AN EYEWEAR ASSEMBLY AND A VEST ASSEMBLY

RELATED APPLICATIONS

This application claims priority under 35 U.S.C. §119(e) from co-pending U.S. Provisional Patent Application No. 61/254,149, filed Oct. 22, 2009, entitled "RETRACTABLE EARPLUG ASSEMBLY FOR AN EYEWEAR ASSEMBLY AND A VEST ASSEMBLY," naming Brauner et al. as inventors, and which is incorporated herein by reference in its entirety and for all purposes.

FIELD OF THE INVENTION

The present invention relates to earplug devices, and more particularly, relates to retractable tether mounted earplug assemblies retrofitted to eyewear and safety vests.

BACKGROUND OF THE INVENTION

It is well known that repeated or prolonged exposure to insalubrious sounds of sufficiently high sound pressure level (SPL) may cause temporary or permanent hearing loss. This is never more apparent than at building construction sites where jackhammers, drilling, and catcalls are sometimes heard simultaneously. Alone, each task can generate a significant sound level, but two or more tasks performed simultaneously can be very detrimental to those close to either event.

Fortunately, earplugs and ear protection devices have been developed that prevent harm to the eardrum and allow individuals to endure extended time in such environments. More recently, high fidelity earplugs have been developed that can be tuned to isolate the ear from certain ranges of high or low frequencies.

While the vast majority of construction workers apply some form of ear protection voluntarily, such ear protection is often mandated by state law or by the construction company itself. Typically, construction workers merely place such ear protection in their pockets or other retrievable region, during nonuse, pulling them out for use when necessary. Such small earplugs, however, are easily lost or misplaced since they often only measure less than an inch in length.

Accordingly, there is a need for various apparel devices that are capable of supporting retractable mounting earplugs.

SUMMARY OF THE INVENTION

The present invention provides an eyewear temple arm apparatus for an eyewear device configured to support a functional element. The temple arm apparatus includes an elongated body member having a proximal end portion that hingeably mounts to the eyewear device. An opposite distal end portion of the elongated body member having a parking structure that defines a cavity therein. The temple arm assembly further includes a functional element, an elongated flexible tether, and a guide base movably mounted to the elongated body member for movement thereof along a fixed path. The base is moved along this path in a direction generally longitudinally along the elongated body between a first position, proximate to a proximal portion of the body member, and a second position, proximate to a distal portion of the body member. One end of the tether is mounted to the guide portion and an opposite end thereof is mounted to the functional element such that when guide base is moved between the first and second positions, the functional element is moved between a parked condition, parked relative to the body member, and an operational condition, positioning the functional element sufficiently away from the body member to enable operation thereof.

Accordingly, an eyewear assembly is provided having retractable functional elements, such as an earplug or clip device, integrally mounted to the temple arms of the eyewear. This is advantageous, in one example, in that usable earplugs can be integrally provided with the eyewear device for use, in the operational condition, that can easily stowed away during periods of non-use, in the parked condition.

In one specific embodiment, the elongated body member defines a passageway extending longitudinally therethrough, distally terminating into the parking structure cavity. The passageway is sized and dimensioned for reciprocal sliding receipt of the tether therein as the guide base is moved between the first position and the second position. The elongated body further defines an elongated slot extending adjacent to, and in communication with, the passageway. This slot being formed and dimensioned for sliding support of the guide base therealong between the first position and the second position.

In another aspect of the present invention, an eyewear assembly is provided which includes an eyewear device, a pair of functional elements, and a pair of temple arms. The temple arms each have an elongated body member with a respective proximal end portion thereof that hingeably mounted at opposed sides of the eyewear device. The eyewear assembly further includes a pair of support mechanisms each cooperating between a respective temple arm and a respective functional element to enable movement thereof between a parked condition and an operational condition. In the parked condition, the function element is parked relative to the respective temple arm, while in the operational condition, the functional element is positioned sufficiently away from the respective temple arm to enable operation thereof.

In one specific configuration, the support mechanisms include a respective elongated flexible tether, each of which cooperates with the respective temple arm for positioning of the tether between a retracted condition and an extended condition. A distal end of each respective tether is mounted to a respective functional element such that when the respective tether is moved between the retracted condition and the extended condition, the respective functional element is moved between the parked condition and the operational condition.

In another embodiment, each temple body member includes an opposite distal end portion thereof that defines a parking structure which is formed and dimensioned for removable receipt of the functional element therein, in the respective parked condition. Each parking structure further includes a respective distal edge portion that defines a respective opening into a respective cavity thereof formed for sliding receipt of the functional element therein.

In still another specific embodiment, the eyewear assembly further includes a pair of guide bases each movably mounted to a respective elongated body member for movement thereof along a respective fixed path in a respective direction generally longitudinally therealong between a respective first position and a respective second position. In the first position, the guide base is positioned proximate to a respective proximal portion of a corresponding body member, while in the second position, the guide base is positioned proximate to a respective distal portion of a corresponding body member. In this configuration, a proximal end of each respective tether is mounted to a respective guide portion such that when the respective guide base is moved between the first and second positions, the respective functional element is moved between a respective parked condition and an respective operational condition. In the parked condition, the functional element is parked relative to the respective body member, while in the operational condition, the element is positioned sufficiently away from the respective body member to enable operation thereof.

In yet another aspect of the present invention, a safety vest assembly is provided including a safety vest, an earplug device, and a retraction mechanism. This mechanism includes an elongated flexible tether device having a distal end thereof mounted to the earplug device element. The retraction mechanism is further movable between a retracted position, parking the earplug device relative to the safety vest, and an extended position, enabling the earplug device to be oriented sufficiently away from the safety vest to enable operation thereof.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawings, in which:

FIG. 1 is a front perspective view of an eyewear assembly incorporating an support mechanism constructed in accordance with the present invention, illustrated in a retracted condition.

FIG. 2 is a rear perspective view of the eyewear assembly of FIG. 1.

FIG. 3 is a bottom perspective view of the eyewear assembly of FIG. 1, with the earplug devices removed.

FIG. 4 is a side elevation of a temple arm of the eyewear assembly of FIG. 1, with the support mechanism in an extended condition.

FIG. 5 is an enlarged, top perspective view of the temple arm of FIG. 4.

FIG. 6 is an enlarged side elevation view of the temple arm of FIG. 4 with one portion of the temple arm removed to expose the passageway thereof.

FIG. 7 is an exploded, top perspective view of the temple arm of FIG. 4, earplug assembly of FIG. 5, in the extended condition.

FIG. 8 is an enlarged, fragmentary, side perspective view of the temple arm of FIG. 6 with the tether device and earplug device removed.

FIG. 9 is a side elevation view, partially broken away, of an earplug device constructed in accordance with another aspect of the present invention.

FIG. 10 is a top perspective view of a central post member for the earplug device of FIG. 9.

FIG. 13 is a top plan view of a retractable reel mechanism for the ear plug assembly for the safety vest of FIG. 11.

FIG. 14 is an exploded top perspective view of the reel mechanism of FIG. 13.

DETAILED DESCRIPTION OF THE INVENTION

Figure 11:
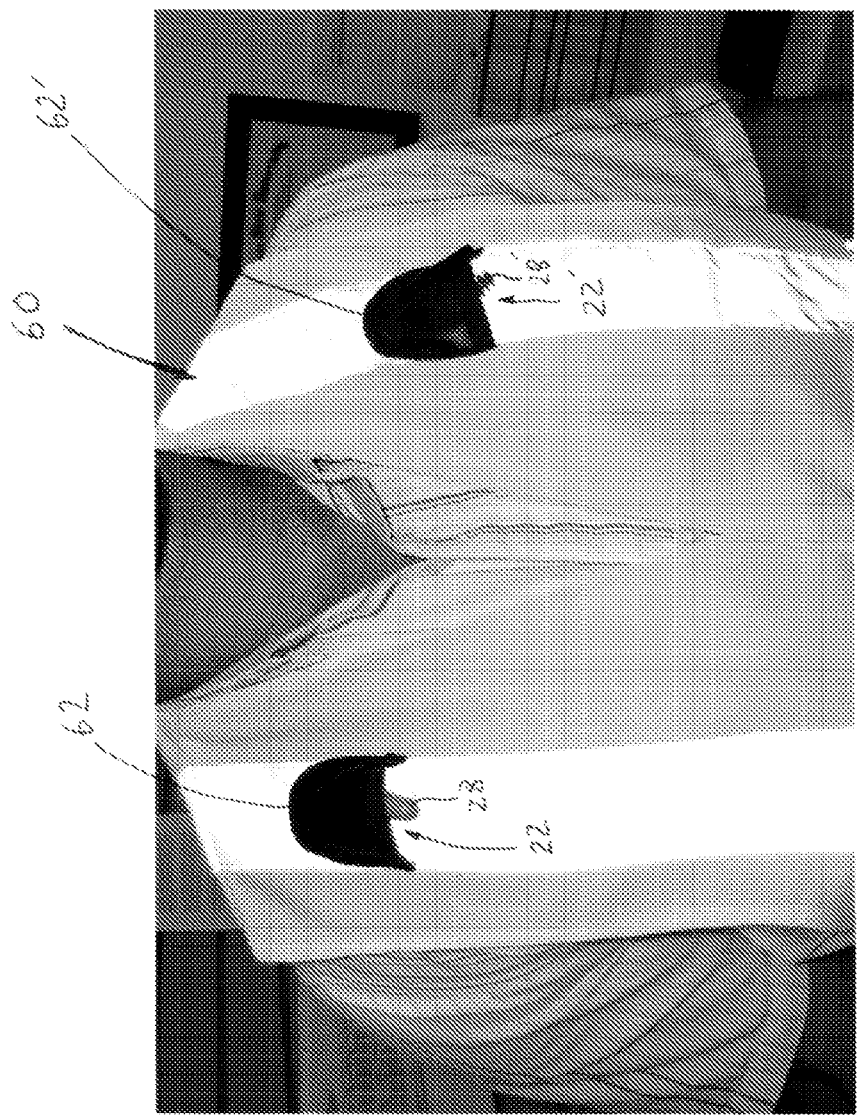
FIG. 11 is a side elevation view of a safety vest incorporated an earplug assembly constructed in accordance with the present invention, and shown in a retracted condition.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to the embodiment of FIGS. 1-8, an eyewear assembly 20 is provided, such as conventional eyeglasses, having eyewear device 21 (framed or unitary piece) that incorporates retractable support mechanisms 22, 22' in the temple arms 23, 23' of the eyewear assembly. Briefly, each support mechanism 22, 22' includes a respective guide base 25, 25' slideably mounted to a corresponding temple arm 23, 23' for selective movement between a first position (FIGS. 1 and 2) and a second position (FIGS. 4-7). More preferably, the guide base 25 configured to slideably cooperate with a guide track 26, 26' integrally formed in a respective temple arm 23, 23', for movement thereof along a fixed path in a direction generally longitudinally therealong between the first position and the second position.

Further, each support mechanism 22, 22' includes a flexible tether device 27, 27' having a proximal end mounted to the slideable guide base 25, 25' and an opposite distal end mounted to a functional 28, 28' element capable of a functional operation. Accordingly, as the slideable guide base 25, 25' is selectively moved between the first position and the second position, the respective functional element 28, 28', via corresponding tethers 27, 27', are moved between a parked condition (FIGS. 1 and 2), enabling parking and storage of the functional elements, and an operational condition (FIGS. 4-7), enabling operational use thereof.

Accordingly, an eyewear assembly 20 is provided having retractable functional elements, such as earplug devices shown in the figures for instance, integrally mounted to the temple arms of the eyewear. This is beneficial in that usable earplugs can be integrally provided with the eyewear device for use, in the operational condition, that can easily stowed away during periods of non-use, in the parked condition. When the guide base 25, 25' moves along the fixed path between the first position (FIGS. 1 and 2) and the second position (FIGS. 4-7), the tether device 27, 27' and the functional elements 28, 28' move between the parked condition (FIGS. 1 and 2) and the operational condition (FIGS. 4-7). As mentioned, in the operational condition, when the eyewear assembly 20 is being worn, the distal end of the flexible tether device 27, 27', in an extended condition, is extended sufficiently away from the corresponding temple arm to enable operational access to the corresponding functional element 28, 28'.

It will be appreciated that the functional elements 28, 28' may be essentially any tool or device that is functional in nature, and that is relatively small so that it is capable of being parked and/or stored adjacent a distal portion of the temple arm. By way of example, such a functional element may be provided by an earplug device, a clip device, and a bottle opener. For illustrative purposes, the however, an earplug device is illustrated in the figures for simplicity.

In the first position, the guide base 25, 25' cooperates with the respective temple arm to position and slideably move the respective tether device 27, 27' along the fixed path, to a retracted condition, wherein the corresponding earplug device 28, 28' is drawn into, or positioned adjacent or proximate to the distal end of the temple arm 23. Accordingly, as shown in FIGS. 1 and 2, in this retracted condition, the tether device 27 does not freely hang or dangle about the hat to prevent entanglement. A much more organized and cleaner appearance is provided. Moreover, this position enables easy access to grip the earplug 28, 28' so that the user can manually pull the earplug device and/or tether toward the extended condition. In the extended condition, of course, the tether is extended from the distal end of the temple arm 23, 23' to enable the earplug device 28, 28' to be placed in the user's ears for use.

Referring now to FIGS. 4-8, only one temple arm 23 with the integrated support mechanism 22 will be described in detail. Briefly, the temple arm apparatus 23 includes an elongated body member 24 having a proximal end portion configured to mount to the eyewear device 21, and an opposite distal end portion thereof defining a parking structure 43 formed and dimensioned for removable receipt of the functional element 28 (e.g., earplug devices) therein.

As mentioned, the guide base 25 of the support mechanism 22 is slideably mounted to the guide track 26 that is integrally formed in the temple arm 23 for movement between the first and second positions. The guide track 26 includes a pair of thin opposed flanges 30, 31 that collectively define an elongated guide slot 32 extending substantially longitudinally along the length of the temple arm 23 between the first and second positions. The guide slot 32 is formed and dimensioned for sliding support of the guide base 25 during movement between the first and second conditions.

Briefly, each guide base 25 includes an upper slide tab portion 33 formed for selective manual manipulation of the base for positioning thereof along the slot 32. In one configuration, the tab portion 33 is substantially rectangular shaped, having a generally flat upper surface that defines a plurality of traction ridges 35 or the like to facilitate gripping manipulation thereof.

The guide base 25 further includes a generally cylindrical-shaped mounting portion 36 positioned below the upper tab portion 33. The mounting portion 36 is connected to, and spaced-apart from, the tab portion 33 by a vertically oriented support wall 37 therebetween. The transverse cross-sectional dimension of the support wall 37, as shown in FIGS. 5 and 8, is sized and formed for sliding receipt in the guide slot 32, permitting reciprocal movement of the guide base 25 therebetween.

The mounting portion 36 of the guide base 25 is formed and dimensioned for sliding receipt in a passageway 40 of the temple arm 23 that extends longitudinally therealong from the first position to the second position. Briefly, this passageway further extends adjacent to, and is in communication with, the guide slot 32. The passageway 40, however, extends to the distal end of the temple arm, via distal end opening 41, whereas the guide slot 32 is narrower in width and does not extend all the way to the distal end. To slidingly accommodate the mounting portion 36 of the guide base, a transverse cross-sectional dimension of the passageway is at least slightly larger than that of the base mounting portion.

The cylindrical mounting portion 36 is further formed to couple to the proximal end of the tether device 27, for selective manipulation of the tether device and mounted earplug between the retracted condition (FIGS. 1 and 2) and the extended condition (FIGS. 4-7), as the guide base is manipulated between the first and second positions, respectively. As best illustrated in FIGS. 6 and 8, in one embodiment, the proximal end may be simply friction fit received in a mounting channel 39 extending longitudinally through the mounting portion 36. Thus, when the guide base 25 is oriented in the first position, the tether device 27 is retracted into, and retained in, the passageway 40, toward the retracted condition. This channel 40, therefore, is not only formed and dimensioned for sliding receipt of the mounting structure therein, but also receives, protects and stores the tether device 27, when oriented in the retracted condition.

To slideably support the guide base 25 along the slot 32 of the guide track 26, as shown in FIGS. 5 and 8, the support wall 37 thereof slides between the opposed flanges 30, 31 of the guide track 26 that define the guide slot 32, while the lower mounting portion thereof slideably engages the passageway.

Briefly, it will be appreciated that while the guide track 26 and guide base 25 could be placed along the bottom or sides of the temple arm 23, the positioning atop the arm is preferred. For one, access to the upper tab portion 33 for operation thereof is easier. Moreover, positioning of the slot 32 at the top of the temple arm will eliminate entanglement, snaring or trapping of the tether in the slot, via gravity, during movement of the guide base.

The tether device 27 is preferably composed of a relatively flexible non-elastic material that provides sufficient tensile strength to secure the earplug device 28 thereto. Such tether flexibility is required to permit operational use of the earplug device 28 when the eyewear assembly 20 is being worn, and when the tether is oriented in the extended condition. Furthermore, the tether must be capable of conforming to the profile of the passageway 40 of the temple arm 23, along the fixed path, when the tether device 27 is moved to the retracted condition. Many cord or strap materials can be satisfactorily employed such as rope, twine, plastic, nylon, and other fabrics. One specific example of the tether material is a tether ribbon composed of fabric. While a non-elastic tether material is preferred, an elastic material can be employed, however.

It will be understood that the extension length of the tether device 27 can be controlled by the length of the fixed path from the first position toward the second position. For example, should the guide track 26 only extend from a proximal portion of the temple arm 23 to a central portion thereof (which incidentally is the orientation shown in FIGS. 4-6 and 8), the extension length of the tether device 27 from the retracted condition to the extended condition will be proportionately shortened. Thus, depending upon the application, the tether extension can be adjusted accordingly. Most preferably, however, the guide slot 32 extends nearly all the way to a distal end of the temple arm 23, providing as long a tether as possible, in the fully extended condition.

In accordance with the present invention, as the guide base 25 moves, slides and/or ratchets along the guide track 26, the tether is retained along the fixed path, substantially eliminating tether dangle. The guide track, in one specific embodiment, is provided by a rail-type structure (i.e., the relatively rigid guide base and guide track) that cooperates with the guide base 25 to move both the guide base and the one end of the tether along the fixed path. In one example, a ratchet type structure may be provided that locks the guide base along the fixed path between the first position and the second position unless the guide base, and hence the tether, is released. Other sliding-type devices suitable for use along the guided fixed path include plastic zippers and enclosed glide and pull devices.

In one specific configuration, the guide slot 32 defines a plurality of nubs or notches 42 spaced apart longitudinally along the slot 32 of the temple arm. These notches function to friction retain the guide base 25 selectively along the temple arm 23 for retainment of the earplug device, at selective extended conditions. The spaced notches 42 are preferably positioned along the top portion of the temple arm, adjacent to the guide slot 32. These notches 42 cooperate with the bottom surface of the upper tab portion 33, in a friction fit manner, to retain the guide base therealong until a manual sliding force, applied to the button portion, is sufficient to overcome the frictional retainment force between the notches 42 and the lower contact surface of the tab.

In one specific embodiment, the distal end of the temple arm 23 includes a parking structure 43 that is formed and dimensioned for at least partial receipt of the functional element (e.g., earplug device 28) therein when the guide base 25 is oriented in the first position, positioning the functional element in the parked condition (FIGS. 1 and 2). In this orientation, a proximal portion of the earplug device is retracted into the parking structure 43, functioning as a protective housing and storage assembly during non-use of the earplug.

As the guide base 25 is manually moved, via the upper tab portion 33, along fixed path of the guide track from the first position, where the tether device 27 is in the corresponding retracted condition (FIGS. 1 and 2), toward the second position, where the tether is moved toward the corresponding extended condition (FIGS. 4-7), the tether is therefore delivered from storage in the passageway 40 through the passageway distal opening 41.

Another technique to deliver the tether is by simply pulling on the earplug device 28, which in turn draws the tether through the passageway distal opening 41 to the retracted condition, and displaces the guide base 25 from the first position to the second position. This provides a sufficient extension or length of tether ribbon to enable mounting of the earplug device 28 to the user's ear.

During periods of non-use, the tether device 27 can be retracted back into the passageway 40 through the passageway distal opening 41. This is performed by manually manipulating the guide base 25, via the upper tab portion 33 along the guide track 26 from the second position (FIGS. 4-7) to the first position (FIGS. 1 and 2). The tether device 27 which is attached to the guide base 25 at the one end, is pulled and retracted back through the passageway distal opening 41 and along the fixed path of the passageway 40 toward the retracted condition.

As best shown in FIGS. 6 and 8, a distal edge portion 44 of the elongated body member 24 defines the opening 41 into a cavity 49 of the parking structure 43 sized and dimensioned for receipt of the functional element 28 therein. This cavity 49 is also communicates with the distal end of the longitudinal passageway 40, enabling reciprocal movement of the tether device 27 in and out of the parking structure 43. The parking structure further includes a distal funnel portion 45 wherein the corresponding portion of the passageway 40 funnels or flares outwardly. This tapered shape and inner diameter of the funnel portion 45 is configured for seated receipt of at least a proximal portion of the earplug assembly therein, by way of example, when the assembly is oriented in the retracted condition. This arrangement, thus, provides protection and storage of the earplug device when not in use.

The flare of the funnel portion 45 accommodates the larger diameter at the proximal portion of the earplug itself. It will be appreciated, however, that the largest diameter of the base of the earplug may be slightly larger than that of the parking structure, due to the compressible nature of most materials used for earplugs. Hence, such compression of the earplugs into the parking structure, when in the retracted condition, helps friction fit retain the earplug therein.

In another aspect of the present invention, detachable earplug assemblies are provided that can be easily attached and detached from the distal end of the tether devices. It will be appreciated that while virtually any earplug device may be mounted to the distal end of the tether device 27, preferably one that is detachable is beneficial. That is, by providing a means for detachable mounting of the earplug device to the distal end of the tether, more sanitary disposable earplug devices may be employed that can be simply and easily replaced and disposed thereof.

Referring now to FIGS. 9 and 10, one embodiment of a detachable earplug device 28 is shown having a conventional foam earplug member 51 that is molded around, and/or adhered to, a generally cylindrical-shaped, rigid, central post member 50. This elongated post member 50 is configured for positioning along a longitudinal axis of the earplug member 51, extending generally from a base proximal end of the earplug to a central portion thereof.

At the proximal end of the post member is a threaded screw member 52 formed for threaded mounting thereto. On a proximal side of the screw member 52 is an eyelet 53 that enables mounting to the tether device 27 or the like, while on a distal side of the screw member 52 is an opposed threaded end. This threaded end is configured for removable threaded mounting in a threaded passage formed in a proximal base portion 55 of the post member 50. This configuration enables removal and replacement of the earplug device 28 via the threaded screw member 52.

The central post member 50, therefore, rather than stiffening, primarily performs the function of providing a platform to mount the threaded screw member 52, as well as retaining the post member 50 to the foam earplug 51, via retaining disks 56 and 57. The post member, however, is relatively rigid in order to sufficiently accommodate the threaded coupling to the screw 52. One particularly suitable material of the post member includes a thermo-elastic polymer material such as plastic or the like, although many other materials, including metal, can be employed. This is beneficial in that the post member 50 is significantly more rugged and easily moldable.

In still another aspect of the present invention, as best shown in FIGS. 11-14, the retractable support mechanism is mounted to a safety vest 60, or the like, used by construction and road workers, for instance. Similar to the other support mechanisms 22, a tether device is provide having one end mounted to a retractor device 61 and the opposite distal end is mounted to the earplug device 28. During operation of the support mechanism 22, tether device 27 and the mounted earplug device 28 are movable between a stored retracted condition (FIG. 11), to protect and store the earplug during non-use, and an extended condition (FIG. 12), enabling operational use of the earplug device.

The support mechanism 22 is preferably housed in a protective pocket 62 or fold oriented at a chest portion of the safety vest 60, forming a protective housing during non-use. This pocket may be facing upwardly, or downwardly, as shown, depending upon the particular use. Access to the support mechanism 22, of course, is though the opening into the protective pocket 62.

Figure 12:
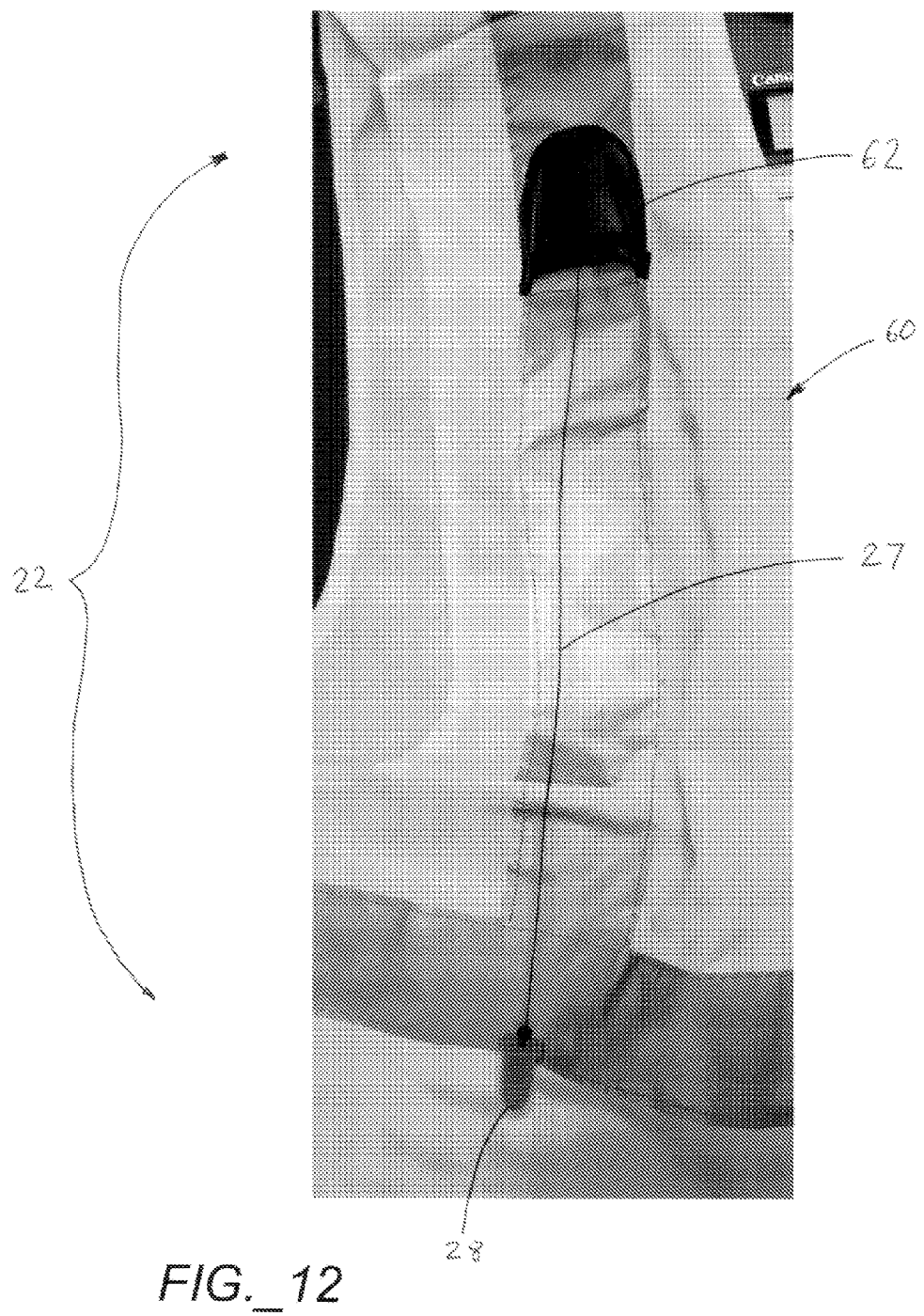
FIG. 12 is a side elevation view of the safety vest of FIG. 11, in an extended condition.

In one particular embodiment, a retrofit support mechanism 22 is provided that incorporates a retractable reel mechanism 63 formed for reeled movement of the tether device 27 between a retracted condition (FIG. 11) and an extended condition (FIG. 12). Due in part to the spooled nature of the reel mechanism 63, a protective housing 65 of the support mechanism 22 is provided that has a significantly smaller footprint than that of the elongated housing embodiments of FIGS. 1-8.

As shown in FIGS. 13 and 14, the protective housing 65 is generally disk-shaped, in all embodiments, having a lower mount support portion 66 and an opposed cover support portion 67. Collectively, the mount support portion 66 and the opposed cover support portion 67 cooperate to define an interior cavity 70 upon which the reel mechanism 63 is rotatably disposed for movement thereof between the first and second positions. The housing 65 further defines a spooling neck portion 71 having an opening 72 into the interior cavity 70. This opening 72 is formed for sliding receipt of the tether device 27 as it reciprocates in and out of interior cavity between the retracted condition and the extended condition.

To retractably spool the tether mounted earplug device 28, a proximal portion of the tether device 27 is mounted to a reel or spool 75 of the retractable reel mechanism 63. As shown in FIG. 14, which illustrates the retractable reel mechanism 63 in general, this spool 75, in turn, is freely rotatably disposed about an axial post member 76 upstanding into the interior cavity 70 from either of the outer covers.

The reel mechanism 63 further includes a coiled torsion spring 77 wound about the axial post member. An inner end of the coiled torsion spring is wedged in a receiving slot 32 of the axial post member 76 of the mount support portion 66, and an opposite outer end is mounted to the spool 75. Thus, by pulling the tether device 27 and/or the earplug device 28 with a force sufficient to overcome the torsional force of the coiled torsion spring 77, the tether device 27 can be extended through the opening 72, causing the mounted earplug device 28 to move from the retracted condition (FIG. 11) to the extended condition (FIG. 12y).

The spool 75 is further caused to rotate around the axial post member 76 as the tether proximal end moves from the first position (FIG. 11) to the second position (FIG. 12). During rotation of the spool 75 about the axial post member 76, in a counter-clockwise direction in FIG. 14, the coiled torsion spring 77 is further tensioned, biasing the spool 75 and the proximal portion of the tether device 27 back toward the first position from the second position. Consequently, the earplug device 28 is moved from the retracted condition to the extended condition, enabling usable access to the earplug device 28.

In one specific embodiment, upon manual release of the tether device 27, the tensioned coiled torsion spring 77 causes the tether device 27 to rewind about the spool 75 back toward the first position. Thus, the reel mechanism 63 will automatically rewind when the force applied to the tether device 27 and/or earplug device 28 or is less than the torsional force of the coiled torsion spring 77.

It will be appreciated that the reel mechanism 63 can be stepped or ratcheted, using conventional ratchet mechanisms (not shown) and techniques. The coiled torsion spring 77, thus, will be unable to rewind the spool 75 back toward the first position unless the ratchet mechanism is released. These ratchet mechanisms thus include a release device to enable manual release from the ratcheting. Conventional release mechanisms include those requiring full extension of the tether device 27, for instance, before a release can commence and allow the spool to rewind the tether. Another example of a release mechanism is to provide an accessible release button 80, such as shown in the specific embodiment of FIG. 13. Operation of this manual release button 80 will release the ratchet mechanism, and enable the torsion spring to rotate the spool 75 and retract/rewind the tether device 27 back to the retracted condition.

In accordance with this embodiment of the present invention, the support mechanism 22 may incorporate single or dual earplug devices 28, although only a single earplug device 28 is mounted to the reel mechanism in the embodiments of FIG. 13-14. One particular reel mechanism is that disclosed in U.S. patent application Ser. No. 12/366,361, to Brauner et al. filed Feb. 5, 2009, and entitled "RETRACTABLE EARPLUG ASSEMBLY FOR A HARDHAT", herein incorporated by reference in its entirety.

Although the present invention has been described in connection with the preferred form of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

What is claimed is:

1. An eyewear temple arm apparatus for an eyewear device, and configured to support an earplug having a proximal portion and a distal portion, said temple arm apparatus comprising:
    an elongated body member having a proximal portion configured to mount to the eyewear device, and an opposite distal portion thereof defining a parking structure having a distal edge portion that defines an opening into a cavity thereof, said cavity defined by an interior wall formed and dimensioned for substantially enclosed, free sliding, peripheral receipt of at least said proximal portion of the earplug therein between an operational condition and a parked condition.

2. The eyewear temple arm apparatus according to claim 1, further including:
    an elongated flexible tether having a distal portion thereof mounted to the earplug, and slideably extending through the parking structure cavity for movement of earplug between the parked condition, slideably parking the earplug within said cavity, and the operational condition, positioning the earplug sufficiently out of the parking structure to enable operation thereof.

3. The eyewear temple arm apparatus according to claim 2, further including:
    a guide base slideably cooperating with said elongated body member for movement thereof along a fixed path in a direction generally longitudinally therealong between a first position, proximate to said body proximal portion, and a second position, proximate to the body distal portion,
    said tether having a proximal portion mounted to said guide base such that when said guide base is oriented at said first position, said earplug is at the parked condition garage, and when said guide base is oriented at said second position, said earplug is at the operational condition.

4. The eyewear temple arm apparatus according to claim 1, further including:
    a guide base slideably cooperating with said elongated body member for movement between a first position and a second position;
    an elongated flexible tether having a proximal portion mounted to the guide base and a distal portion thereof mounted to the earplug;
    wherein said elongated body member defines a passageway extending longitudinally therethrough and distally terminating at the parking structure cavity, said passageway being sized and dimensioned for reciprocal sliding receipt of said tether therein as the guide base is moved between the first position and the second position.

5. The eyewear temple arm apparatus according to claim 4, wherein
    said elongated body further defines an elongated slot extending adjacent to, and in communication with, said passageway, said slot being formed and dimensioned for sliding support of said guide base therealong between the first position and the second position.

6. The eyewear temple arm apparatus according to claim 1, wherein
said parking structure is generally conical-shaped.

7. An eyewear temple arm apparatus for an eyewear device comprising:
an elongated body member having a proximal portion configured to mount to the eyewear device, and defining a passageway extending longitudinally therethrough and distally terminating at a distal portion of the body member, said body member further defining an elongated slot extending from an exterior surface thereof into said passageway, and extending longitudinally therealong;
a functional element;
an elongated flexible tether; and
a guide base slideably mounted in said elongated slot of said elongated body member for accessible, selective movement and positioning thereof along a fixed path in a direction generally longitudinally therealong between a first position, proximate to a proximal portion of the body member, and a second position, proximate to a distal portion of the body member,
wherein one end of said tether is mounted to said guide base and an opposite end thereof is mounted to said functional element such that when guide base is moved along said elongated slot between the first and second positions, said functional element is moved between a parked condition, parked relative to the body member, and an operational condition, positioning the functional element sufficiently away from the body member to enable operation thereof.

8. The eyewear temple arm apparatus according to claim 7, wherein
said functional element is an earplug.

9. An eyewear assembly comprising:
an eyewear device;
a pair of temple arms each having an elongated body member having respective proximal portion thereof hingeably mounted at opposed sides of the eyewear device;
a pair of functional elements; and
a pair of support mechanisms each cooperating between a respective temple arm and a respective functional element to enable movement thereof between a parked condition, parked relative to the respective temple arm, and an operational condition, positioning the functional element sufficiently away from the respective temple arm to enable operation thereof
each said support mechanism including a respective elongated flexible tether, each cooperating with the respective temple arm for positioning between a retracted condition and an extended condition, a distal end of each respective tether being mounted to a proximal portion of each respective functional element such that when the respective tether is moved between the retracted condition and the extended condition, the respective functional element is moved between the parked condition and the operational condition;
each temple body member includes an opposite distal portion thereof defining a parking structure having a longitudinal axis aligned generally in the longitudinal direction of the elongated body member, and formed and dimensioned for sliding removable receipt of at least said proximal portion of the functional element therein, in the respective parked condition.

10. The eyewear assembly according to claim 9, wherein said parking structure is generally conical-shaped.

11. The eyewear assembly according to claim 9, wherein each said parking structure includes a respective distal edge portion that defines a respective opening into a respective cavity thereof formed for sliding receipt of the functional element therein.

12. The eyewear assembly according to claim 9, further including:
a pair of guide bases each movably mounted to a respective elongated body member for movement thereof along a respective fixed path in a respective direction generally longitudinally therealong between a respective first position, proximate to a respective proximal portion of a corresponding body member, and a respective second position, proximate to a respective distal portion of a corresponding body member,
wherein a proximal end of each respective tether is mounted to a respective guide portion such that when the respective guide base is moved between the first and second positions, the respective functional element is moved between a respective parked condition, parked relative to the respective body member, and an respective operational condition, positioning the functional element sufficiently away from the respective body member to enable operation thereof.

13. The eyewear assembly according to claim 12, wherein each said elongated body member defines a respective passageway extending longitudinally therethrough and distally terminating at the body distal portion, said passageway being sized and dimensioned for reciprocal sliding receipt of said tether therein between the respective retracted condition and the respective extended condition as the respective guide base is moved between the first position and the second position.

14. The eyewear assembly according to claim 13, wherein each said elongated body member further defines a respective elongated slot extending adjacent to, and in communication with, the respective passageway, each said slot being formed and dimensioned for sliding support of the respective guide base therealong between the respective first position and the respective second position.

15. The eyewear assembly according to claim 9, wherein said functional element is an earplug.

16. An eyewear temple arm apparatus for an eyewear device, and configured to support a functional element, said temple arm apparatus comprising:
an elongated body member having a proximal portion configured to mount to the eyewear device, and an opposite distal portion thereof defining a parking structure formed and dimensioned for removable receipt of the functional element therein.
a guide base slideably cooperating with said elongated body member for movement between a first position and a second position; and
an elongated flexible tether having a proximal portion mounted to the guide base and a distal portion thereof mounted to the functional element;
wherein said elongated body member defining a passageway extending longitudinally therethrough and distally terminating at the parking structure cavity, said passageway being sized and dimensioned for reciprocal sliding receipt of said tether therein as the guide base is moved between the first position and the second position; and
wherein said elongated body further defines an elongated slot extending adjacent to, and in communication with, said passageway, said slot being formed and dimensioned for sliding support of said guide base therealong between the first position and the second position.

17. The eyewear temple arm apparatus according to claim 16, wherein
said parking structure includes a distal edge portion that defines an opening into a cavity thereof formed for sliding receipt of at least a proximal portion of the functional element therein.

18. The eyewear temple arm apparatus according to claim 16, wherein
said guide base slideably cooperating with said elongated body member for movement thereof along a fixed path in a direction generally longitudinally therealong between said first position, proximate to said body proximal portion, and said second position, proximate to the body distal portion,
said tether having a proximal end mounted to said guide base such that when said guide base is oriented at said first position, said functional element is at the parked condition garage, and when said guide base is oriented at said second position, said functional element is at the operational condition.

19. An eyewear temple arm apparatus for an eyewear device, and configured to support an earplug having a proximal portion and a distal portion, said temple arm apparatus comprising:
an elongated body member having a proximal portion configured to mount to the eyewear device, and an opposite distal portion thereof defining a parking structure having a longitudinal axis aligned generally in the longitudinal direction of the distal portion of the elongated body member, said parking structure includes a distal edge portion that defines an opening into a cavity thereof formed for sliding axial receipt of the at least said proximal portion of the earplug; and
an elongated flexible tether having a distal portion thereof mounted to the earplug, and slideably extending through the parking structure cavity for movement of earplug between a parked condition, slideably parking the earplug within said cavity, and an operational condition, positioning the earplug sufficiently out of the parking structure to enable operation thereof.

20. The eyewear temple arm apparatus according to claim 19, further including:
a guide base slideably cooperating with said elongated body member for movement between a first position and a second position;
an elongated flexible tether having a proximal end mounted to the guide base and a distal portion thereof mounted to the earplug;
wherein said elongated body member defines a passageway extending longitudinally therethrough and distally terminating at the parking structure cavity, said passageway being sized and dimensioned for reciprocal sliding receipt of said tether therein as the guide base is moved between the first position and the second position.

21. The eyewear temple arm apparatus according to claim 20, wherein
said elongated body further defines an elongated slot extending adjacent to, and in communication with, said passageway, said slot being formed and dimensioned for sliding support of said guide base therealong between the first position and the second position.

22. The eyewear temple arm apparatus according to claim 19, wherein
said parking structure is generally conical-shaped.

* * * * *